(12) United States Patent
Suehling et al.

(10) Patent No.: US 11,730,440 B2
(45) Date of Patent: Aug. 22, 2023

(54) METHOD FOR CONTROLLING A MEDICAL IMAGING EXAMINATION OF A SUBJECT, MEDICAL IMAGING SYSTEM AND COMPUTER-READABLE DATA STORAGE MEDIUM

(71) Applicant: Siemens Healthcare GmbH, Erlangen (DE)

(72) Inventors: Michael Suehling, Erlangen (DE); Andreas Wimmer, Forchheim (DE); Stefanie Steding, Zirndorf (DE); Christian Hofmann, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/826,277

(22) Filed: May 27, 2022

(65) Prior Publication Data

US 2022/0378391 A1    Dec. 1, 2022

(30) Foreign Application Priority Data

May 31, 2021 (EP) .................................... 21176876

(51) Int. Cl.
*A61B 6/00* (2006.01)
*A61B 6/04* (2006.01)

(52) U.S. Cl.
CPC ............ *A61B 6/547* (2013.01); *A61B 6/0407* (2013.01); *A61B 6/4028* (2013.01);
(Continued)

(58) Field of Classification Search
CPC ...... A61B 6/547; A61B 6/0407; A61B 6/0487
See application file for complete search history.

(56) References Cited

U.S. PATENT DOCUMENTS

2016/0256223 A1* 9/2016 Haimerl ................. A61B 34/20
2020/0205748 A1 7/2020 Pautsch et al.
(Continued)

FOREIGN PATENT DOCUMENTS

CN       105411617 A    3/2016
CN       111374675 A    7/2020
(Continued)

OTHER PUBLICATIONS

Welch, G.; Bishop, G.:"An Introduction to the Kalman Filter", Sep. 17, 1997.
(Continued)

*Primary Examiner* — Dani Fox
(74) *Attorney, Agent, or Firm* — Harness, Dickey & Pierce, P.L.C.

(57) ABSTRACT

The method comprises receiving an image sequence of the subject from the camera during the medical imaging scan; receiving at least one of the current position or velocity of the patient table during the medical imaging scan; performing a motion tracking analysis of the image sequence to extract a motion model, wherein at least one of the motion tracking analysis or the motion model is tailored to the body region of interest and takes into account the at least one of the current patient table position or velocity; and analysing the motion model to detect subject motion and, if the detected motion is above a threshold, at least one of adapting the medical imaging examination or issuing an alert.

19 Claims, 4 Drawing Sheets

(52) U.S. Cl.
CPC .......... *A61B 6/4035* (2013.01); *A61B 6/4275* (2013.01); *A61B 6/4441* (2013.01)

(56) References Cited

U.S. PATENT DOCUMENTS

| | | |
|---|---|---|
| 2020/0219254 A1 | 7/2020 | Regensburger et al. |
| 2020/0268251 A1 | 8/2020 | Hao et al. |
| 2020/0268339 A1* | 8/2020 | Hao .................. G06T 7/0014 |
| 2020/0323496 A1 | 10/2020 | Eibenberger et al. |

FOREIGN PATENT DOCUMENTS

| | | |
|---|---|---|
| CN | 111402144 A | 7/2020 |
| WO | WO 2019173237 A1 | 9/2019 |

OTHER PUBLICATIONS

Barron, J.; Fleet, D.; Beauchemin, S.: "Performance of Optical Flow Techniques", in: International Journal of Computer vi-sion 12, 43-77 (1994).

Google MediaPipe (currently available under hups://mediapipe.dev) (Stand: 12.05.2021).

Schäfer, Dirk et al. "Motion-Compensated and Gated Cone Beam Filtered Back-Projection for 3-D Rotational X-Ray Angiography" IEEE Transactions on Medical Imaging, vol. 25, No. 7, pp. 898-906, Jul. 2006; 2006.

European Extended Search Report dated Dec. 14, 2021.
European Intention to Grant dated Dec. 21, 2022.

\* cited by examiner

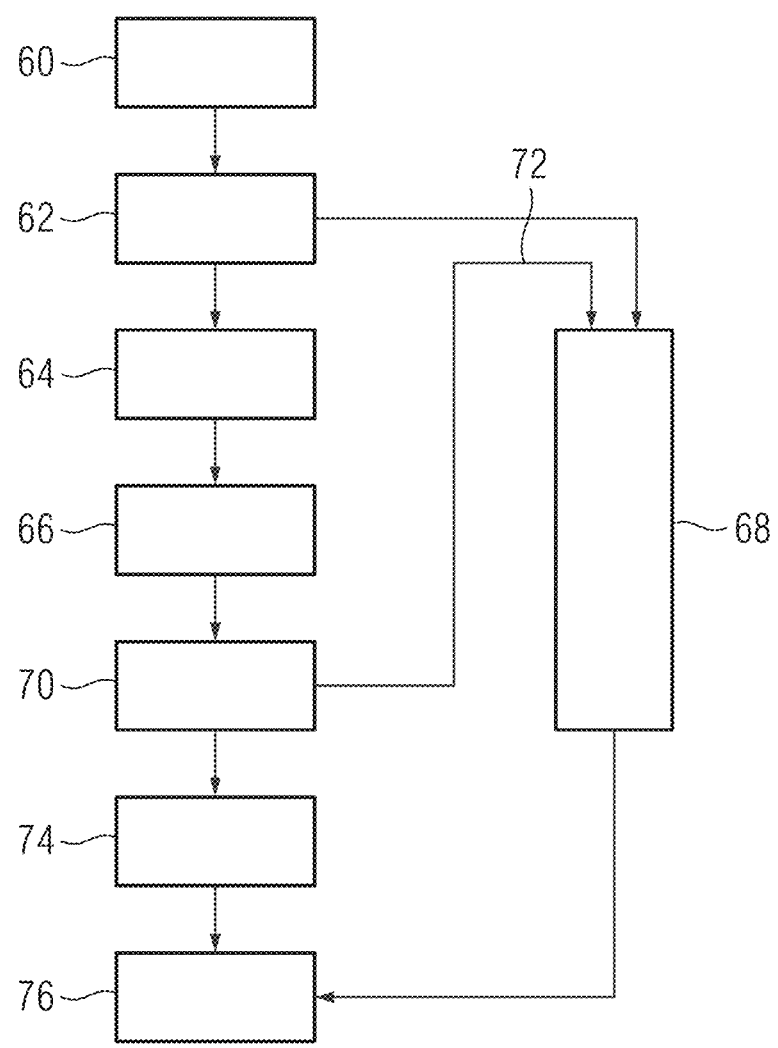

METHOD FOR CONTROLLING A MEDICAL IMAGING EXAMINATION OF A SUBJECT, MEDICAL IMAGING SYSTEM AND COMPUTER-READABLE DATA STORAGE MEDIUM

CROSS-REFERENCE TO RELATED APPLICATION(S)

The present application claims priority under 35 U.S.C. § 119 to European Patent Application No. EP 21176876.7, filed May 31, 2021, the entire contents of which are incorporated herein by reference.

FIELD

Embodiments of the present invention relate to a method for controlling a medical imaging examination of a subject, a medical imaging system having a gantry, a patient table which is moveable with respect to the gantry, a camera disposed above the patient table and a control unit, and a non-transitory computer-readable data storage medium.

BACKGROUND

Despite the huge progress in medical imaging acquisition speed, patient motion such as breathing or unintended body movements still cause motion-induced image artefacts. In the present clinical routine, patients are asked not to move or to hold their breath for a period of time during the medical imaging scan. However, this poses a challenge to a number of patients who are not able to comply with this because of their health impairments. Hence, there is need that the medical imaging system adapts to the patient motion. There already exist some algorithms to compensate for motion in the medical image reconstruction, for example D. Schäfer, J. Borgert, V. Rasche and M. Grass "Motion-Compensated and Gated Cone Beam Filtered Back-Projection for 3-D Rotational X-Ray Angiography", IEEE Transactions on Medical Imaging, vol. 25, no. 7, July 2006. However, this motion correction reconstruction method assumes that a motion vector for every voxel is known.

SUMMARY

The inventors have identified that it is a challenge is to track and quantify the patient motion during a scan. For respiratory motion tracking, simplified measurement systems exist, such as fixation belts to position a pressure transducer, or laser scanners. However, the inventors have determined that these devices complicate the scan workflow and are mainly used for therapy-related imaging such as radiation therapy planning, as they are too complex for routine clinical images.

Embodiments of the present invention provide a simpler approach to track and quantify patient motion, which does not place a burden or take up time of the operating staff of the medical imaging system. Embodiments of the present invention also more adequately adapt the medical imaging examination to the estimated patient motion.

An embodiment of the present invention provides a method for controlling a medical imaging examination of a subject, wherein the medical imaging examination comprises performing a medical imaging scan of a body region of interest of the subject using a pre-selected scan protocol, wherein the medical imaging examination is performed using a medical imaging system having a gantry, a patient table which is moveable with respect to the gantry and on which the subject is positioned, a control unit for controlling the medical imaging scan and having access to an image sequence of the subject acquired by a camera, and wherein the method comprises the steps of receiving an image sequence of the subject from the camera during the medical imaging scan; receiving the current position and/or velocity of the patient table during the medical imaging scan; performing a motion tracking analysis of the received image sequence to extract a motion model, wherein the motion tracking analysis and/or the motion model is tailored to the body region of interest and takes into account the current patient table position and/or velocity; analysing the motion model to detect subject motion and, for example if the detected motion is above a pre-determined threshold, adapting the medical imaging examination to the detected motion and/or issuing an alert to make the subject and/or an operator of the medical imaging system aware of the detected motion.

The method uses a camera-based approach to track and quantify patient motion and further uses the intrinsic knowledge of the system about the scan protocol and/or the motion of the patient table to adequately adapt the medical imaging examination to the estimated patient motion.

The medical imaging examination may be any clinical medical imaging exam, including angiography or radiation therapy planning. The medical imaging examination may comprise one or several medical imaging scans, wherein each medical imaging scan acquires medical images from a body region of interest of the subject using a pre-selected scan protocol. The scan protocol may be pre-selected by the radiologist or a doctor ordering the medical imaging examination and may already specify the body region of interest, as well as scan parameters. The scan parameters may include the resolution, slice thickness, dose, radiation energy and whether or not contrast agent is to be applied. Thus, the scan protocol may be tailored to the diagnostic question (for example trauma, tumour, blood vessels, stroke), as well as the body region of interest on which the medical imaging scan is to be performed.

The medical imaging system has a gantry and a patient table which is moveable with respect to the gantry and on which the subject is lying, usually in a supine position. According to an embodiment, the gantry comprises an X-ray source and an X-ray detector, which are rotatable around the patient table. According to an embodiment, the gantry comprises a superconducting magnet in form of a hollow cylinder, into which the patient table can be inserted along an axial direction.

In some embodiments, the gantry is stationary, and the patient table is moveable at least in axial direction (z-direction) through the gantry. However, embodiments of the present invention are also applicable to medical imaging system with a moveable, e.g., slidable, gantry, wherein the patient table may be stationary or may also be moveable. Gantry and patient table are usually moveable at least in z-direction with respect to each other. The medical imaging system further comprises a control unit for controlling the medical imaging scan, which may be part of a computer system. The control unit has access to image sequences acquired by a camera disposed above the subject. The motion tracking analysis according to embodiments of the present invention may also be performed by the control unit, or by another processing unit, which may also be part of the computer system and which is connected via a data link to the control unit. Thus, the processing unit may be the or part of the control unit.

The camera may be fixed to the gantry and may be integrated into the medical imaging system. It may be disposed somewhere above the patient table. It may be mounted on a separate stand or at the ceiling above the patient table. Thus, the camera may be stationary with respect to the gantry, or alternatively with respect to the patient table. The camera may be an optical camera, in particular a digital or video camera capable of acquiring a time sequence of images of the patient while he is positioned on the patient table. The time resolution is preferably sufficient to capture relevant movement during the scan, for example 2-120 frames per second. The camera may be a camera already integrated in state-of-the art medical imaging systems, which today is used simply for visual patient monitoring. According to embodiments of the present invention, the control unit receives not only the image sequence from the camera during the medical imaging scan but is also aware of or receives the current position and/or velocity of the patient table, and optionally also the pre-selected scan protocol.

The control unit or processing unit then performs a motion tracking analysis of the received image sequence to extract a motion model of the body region of interest of the subject, wherein the motion tracking analysis and/or the motion model are tailored to the body region of interest and take into account the current patient table position and/or velocity. Thereby, the motion tracking analysis may be simplified and therefore stabilized, because based on the body region of interest and optionally the scan protocol to be applied, an appropriate, e.g., simplified motion model is applied. Already knowing the body region of interest also allows to detect the relevant body region on the images (which may have a larger field of view) beforehand.

In the next step, the motion model is analysed to detect subject motion. Preferably, the detected motion is classified as sufficient to compromise the scan process (e.g., above a pre-determined threshold) or as non-existent or irrelevant. For example, if the threshold is crossed (or always), the medical imaging system may adapt to the motion in a manner specific to the medical imaging examination and optionally scan protocol and/or body region.

Thus, a camera-based approach is presented to track and quantify patient motion and to adequately adapt the medical imaging examination to the estimated patient motion. The method exploits specific information available at the medical imaging system, such as the body region to be scanned and optionally the scan protocol to be applied, in order to adequately react to patient motion. The method also incorporates available motion information of the patient table. Embodiments of the present invention, thus, provide a method for mitigating the effect of patient motion, in which the scan workflow is not negatively impacted by additional devices or workflow steps to track patient motion.

The motion tracking analysis may utilise machine-learning based algorithms to estimate motion on the image sequence. For example, algorithms provided by Google MediaPipe (currently available under https://mediapipe.dev) may be used. The algorithms use e.g., neural networks, to extract the position of pre-determined objects on each image. Thereby, motion can be estimated directly from the RGB image data, or in the case of a three-dimensional (3D) camera acquiring images with depth information, also form the depth data. In low-end medical imaging systems, where only two-dimensional (2D) cameras are available, the motion tracking analysis may include deriving the motion from the 2D image sequences using a state-of-the art algorithms. By taking into account the current patient table position and/or velocity, the motion may be corrected for movements of the medical imaging system patient table, that are explicitly known within the control unit. One correction approach is to subtract the table motion from the camera-estimated overall motion. This ensures that only patient motion relative to the table is captured by the camera-based motion estimates.

According to an embodiment, the motion tracking analysis uses a motion model which is specific to the selected scan protocol and/or the body region of interest. In some embodiments, the selected scan protocol already comprises the relevant body region, wherein the body region of interest may for example be head, thorax, a limb or part of a limb, hip, neck, shoulder, or any other body part which may be covered by a medical imaging scan. The motion model may be tailored to the shape, the features and/or the kind of motion that may occur in the specific body region. In particular, the motion model may consider the joints and the movement they allow. For example, the head may, in a first approximation, be taken as a rigid body, i.e., it can rotate and possibly translate, but the skull cannot deform within itself. In a second approximation, movements of the jaw and throat, such as swallowing, may be incorporated into the model. Motion models of the limbs may incorporate the possible movement at the joints, whereas a motion model of the thorax will include breathing motion and optionally the heartbeat. Thus, the motion tracking analysis will specifically look out for motion which fits the motion model specific to the body region of interest to be scanned.

The default/general motion model may be a dense, elastic motion field capturing the motion at each image position.

When the motion model is specific to the body region of interest, the motion tracking analysis may comprise detecting and tracking landmarks specific to the body region of interest in the image sequence, applying a filter algorithm to the tracked landmarks to compensate inaccurate detections in one or several of the images of the sequence, in particular a Kalman filter; correcting the tracked landmarks by the position and/or velocity of the patient table; and estimating the motion model based on the filtered and corrected landmarks.

The landmarks can be detected for example by an algorithm based on a trained neural network. Thus, an appropriate number of landmarks (e.g., 6-300, preferably 40-150) may be pre-defined for each specific body region, wherein the landmarks designate characteristic portions of the body surface. If the body region is the head, the landmarks may be facial landmarks, which may be used to determine the position of the eyes, nose, and mouth.

Since the landmarks are detected in each image of the sequence independently of each other, errors in the detection may lead to abrupt changes from on image to the next, leading to instability. Therefore, a filter algorithm may be applied to the tracked landmarks to compensate inaccurate detections in one or several of the images. In one embodiment, this may be a Kalman filter, as described for example in G. Welch and G. Bishop "An Introduction to the Kalman Filter", Sep. 17, 1997. A Kalman filter is an algorithm that uses a series of measurements observed over time (here: the positions of the tracked landmarks) containing statistical noise and other inaccuracies, to produce estimates of unknown valuables (here: the positions of tracked landmarks on later/future images in the series) that tend to be more accurate than those based on a single measurement alone. By using a Kalman filter, the motion of the tracked landmarks can be estimated with higher certainty and stability. An alternative algorithm is the Sparse Optical Flow algorithm, for example, as described in J. Barron, D. Fleet and S. S. Beauchemin "Performance of Optical Flow Techniques", International Journal of Computer vision 12, 43-77 (1994). This technique may be used to approximate the 2D motion field, i.e., the projection of 3D velocities onto the imaging surface, from the image intensity of the image sequence.

Since the subject motion is being tracked during a medical imaging scan, table movement is expected. To ensure that only the movement of the body region of interest, for example the head, is detected, the positions of the tracked landmarks may be corrected according to the patient table movement. These table movements (position and/or velocity including the direction) are explicitly known within the medical imaging system, e.g., in the control unit. Thus, based on the filtered and corrected landmarks, a motion model specific to the body region can be estimated. In an embodiment, the motion vectors of the landmarks constitute the motion model.

According to an embodiment, the motion tracking analysis further comprises estimating rotation and translation vectors on the basis of the positions of the landmarks on each image of the sequence and the camera parameters, determining the orientation and movement of the body region of interest, in particular the head, based on the detected landmarks and the rotation and translation vectors. From the position of the landmarks and the known intrinsic parameters of the camera, in particular the camera's position and orientation with respect to the patient table, rotation and translation vectors can be estimated. These translation and rotation vectors may for example apply to a body region which may be assumed to be a rigid body, such as the head. In this case, only 6 degrees of freedom (three translation vectors and the three Euler angles) need to be estimated for each time point.

For this purpose, a direct linear transform solution with the known intrinsic parameters of the camera could be applied. In this process, each landmark of the body of interest in the world coordinate system is projected onto the image plane to consider the orientation and position of the body from an image sequence to the camera. To minimize projection errors, a Levenberg-Marquart optimisation could be applied to iteratively adjust the rotation and translation vectors. Furthermore, the resulting vectors and the intrinsic parameters of the camera may be used to calculate the Euler angles. Consequently, the orientation and movement of the head may be checked based on the determined facial landmarks, vectors and angles.

According to an embodiment, the method comprises a step of correcting the motion model or the motion vector field by the patient table velocity. This may be done by correcting the motion model, in particular the position for the landmarks and motion vectors, by estimating the translation using the current position and/or velocity of the patient table. Thereby, the table motion in the images in the images may be compensated by shifting the image content by the table motion. Further, the control unit may identify the current patient table position, and only once the table position is close to the target position for the examination, the motion tracking analysis is started. In another embodiment, the threshold for motion recognition may be corrected by the patient table velocity.

According to an embodiment, the motion tracking analysis is started only once the patient table has reached a target position for the examination. Usually, the patient will lie down on the patient table while it is disposed outside the gantry, and then the patient table will be shifted at least in z-direction into the gantry, to a target position for this examination, e.g., such that the body region of interest is inside the gantry. By starting the motion tracking approach only once the patient table is at the target position, the calculation effort for correcting fast table motion may be reduced.

In the event that the body region is the thorax, the motion tracking analysis may comprise the extraction of a one-dimensional (1D) model of upwards and downwards motion of the thorax from the image sequence acquired by a three-dimensional camera. This implies that depth information is available, and in this case the upward/downward motion may provide an adequate model of breathing. For example, the motion tracking analysis may comprise a step of averaging the depth (i.e., distance from the camera) of the chest over a pre-defined area on each image of the sequence, and optionally using a Kalman filter to predict the further breathing motion. Since the breathing motion is cyclic, extrapolation of the movement is possible.

The motion tracking analysis may comprise a step of applying a dense motion tracking approach to the sequence of images to estimate a motion vector field, in particular by using an optical flow technique. This approach is advantageous in particular in case only 2-D camera motion tracking is available. This may be followed by correcting the motion vector field by the patient table velocity. From the motion field, the breathing motion may be extracted as follows:

According to an embodiment, the motion vector field is calculated first in a coarse resolution, followed by a calculation by one or several finer resolutions. In other words, the analysis may be performed in a multi-resolution fashion to obtain a global breathing model at a coarse level, but and detect further movements at the finer resolutions. In an example, the image sequence may have a resolution of 640×1080 pixels. However, in the first step, it is sampled to a much lower resolution, in order to estimate motion on a large scale first. This has the advantage that aliasing is suppressed. When the main movements have been identified, the analysis is repeated on a finer resolution, to further differentiate detected motion.

According to an embodiment, the motion tracking analysis may further comprise the steps of analysing the orientation of the motion vector field for detecting inward and outward motion, in particular by calculating the divergence of the motion vector field, and on this basis estimating a motion model of breathing motion.

This is based on the insight that inspiration and expiration can be differentiated by analysing the orientation of the motion vectors: at the sides of the body, inspiration, i.e., an expansion of the chest, is characterized by motion vectors pointing towards the boundaries of the image. During expiration, i.e., contraction of the chest, the motion vectors point towards the centre. Mathematically, this may be characterised by the divergence of the vector field, a positive value indicates an expansion of the chest (inspiration), a negative value indicating expiration.

Further, a secondary breathing motion in z-direction may be observed in the waist region or the shoulder region. For the shoulders, inspiration leads to a shift towards the head, whereas expiration leads to a movement towards the feet. At the waist, the motion may be upwards or downwards for inspiration, depending on whether chest or abdominal breathing is dominant. Nevertheless, the movement in z-direction at the waist may be valuable to support the detection of breathing and to differentiate between chest and abdominal breathing if the general phases of inspiration/expiration are detected from the body sides or the shoulders. The magnitude of the motion vector field describes the amount of breathing motion. The above-described multi-resolution analysis may be used to be able to differentiate between abdominal and chest breathing in the finer resolutions.

Based on the detected motion, in particular whether the motion crosses a threshold, the medical imaging system may react and adapt the medical imaging examination in on or more ways.

According to an embodiment, the medical imaging system may issue an alert to the subject and/or the operator. For example, the operator, i.e., a technician or radiological assistant, may receive a visual or acoustic warning. The visual warning can be realized as a colour overlay on the live image shown on the scanner tablet. The alert may include the kind of detected motion, and suggestions for action. For example, to re-position the patient, or to instruct the patient to counteract the movement. Alternatively, the subject may be made aware of the motion through a visual or acoustic warning. According to an embodiment, the alert issued to the subject may comprise the kind of motion and/or a suggestion for correcting the motion. For example, the alert may include a visual or acoustic sign to catch the subject's attention. Afterwards, one or more of the images acquired by the camera may be displayed to the subject on a screen, including arrows to indicate how the patient should move in order to correct the inadvertent motion. For example, there may be an arrow or an acoustic sign, asking him to turn his head back to the centre, when he/she before turned the head to one side.

According to another embodiment, adapting the medical imaging examination may comprise re-acquiring the medical imaging data which were compromised by the detected motion. The medical imaging data may be, for example, computed tomography data or magnetic resonance imaging data.

For example, the patient table may stop or move backwards to allow the medical imaging system to scan the affected portions again. This may be necessary for example when coughing is detected, which is possible using the inventive technique. In prior art techniques, only a respiratory surrogate (i.e., a simplified 1D signal) was detected via the chest belt, and this could not detect complex movement like coughing. By detecting couching in the camera-based inventive approach, re-scanning of certain z-positions may be triggered when necessary.

According to a further embodiment, adapting the medical imaging examination may comprise performing a motion-compensated image reconstruction of the medical imaging data (also referred to as motion-compensated medical image reconstruction), for example a motion-compensated filtered-back projection. In other words, the camera-based motion estimation may be used as input information for state-of-the-art motion-compensated reconstruction algorithms, like the algorithm by Dirk Schafer mentioned above, to correct the reconstruction for the estimated motion. The medical image reconstruction may be, for example, a computed tomography image reconstruction or a magnetic resonance image reconstruction.

According to an embodiment, the medical imaging examination is a computed tomography examination (also referred to as a CT examination), the medical imaging scan is a computed tomography scan (also referred to as a CT scan), and the medical imaging system is a computed tomography system (also referred to as a CT system).

In particular, a method for controlling a CT examination of a subject is disclosed herewith, wherein the CT examination comprises performing a CT scan of a body region of interest of the subject using a pre-selected scan protocol, wherein the CT examination is performed using a CT system having a gantry, a patient table which is moveable with respect to the gantry and on which the subject is positioned, a control unit for controlling the CT scan and having access to an image sequence of the subject acquired by a camera, and wherein the method comprises the steps of (a) receiving an image sequence of the subject from the camera during the CT scan;

(b) receiving the current position and/or velocity of the patient table during the CT scan;

(c) performing a motion tracking analysis of the received image sequence to extract a motion model, wherein the motion tracking analysis and/or the motion model is tailored to the body region of interest and takes into account the current patient table position and/or velocity;

(d) analysing the motion model to detect subject motion and, for example if the detected motion is above a pre-determined threshold, adapting the CT examination to the detected motion and/or issuing an alert to make the subject and/or an operator of the CT system aware of the detected motion.

According to an embodiment, the medical imaging examination is a magnetic resonance imaging examination (also referred to as an MRI examination), the medical imaging scan is a magnetic resonance imaging scan (also referred to as an MRI scan), and the medical imaging system is a magnetic resonance imaging system (also referred to as an MRI system).

Embodiments of the present invention are further directed to a medical imaging system comprising a gantry, a patient table which is moveable with respect to the gantry, a camera disposed above the patient table in a known position and orientation with respect to the gantry, wherein the camera is adapted to acquire an image series of a subject positioned on the patient table, and a control unit for controlling a medical imaging scan. The control unit is adapted to receive an image sequence of the subject from the camera during the medical imaging scan, and the current position and/or velocity of the patient table during the medical imaging scan. The control unit is further adapted for performing a motion tracking analysis of the received image sequence to extract a motion model, wherein the motion tracking analysis and/or the motion model is tailored to the body region of interest and takes into account the current patient table position and/or velocity; and the control unit is further adapted for analysing the motion model to detect subject motion and, for example if the detected motion is above a pre-determined threshold, for adapting the medical imaging examination to the detected motion and/or for issuing an alert to make the subject and/or an operator of the medical imaging system aware of the detected motion.

The medical imaging system is adapted for performing the method according to embodiments of the present invention. All features and advantages described with respect to the method are also applicable to the medical imaging system and vice versa. The method may be (at least partly) carried out by a control unit, which is part of the medical imaging system, and which receives the image sequence, performs the motion tracking analysis, and may adapt the medical imaging examination to react to the detected motion.

According to an embodiment, the camera is a video camera or digital camera adapted to acquire 2-D. The camera may be integrated into the gantry. Thereby, the position and other intrinsic camera parameters, such as the field-of-view, the imaging angle with respect to the patient table, the resolution, etc. are automatically known to the medical imaging system, in particular the control unit.

According to an alternative embodiment, the camera inside is a 3D camera adapted to acquire images including depth information of the subject. Such 3D cameras may for example include two lenses in order to capture the body region of interest in two angles, and thereby extract contour/depth information.

The medical imaging system may be, for example, a computed tomography (CT) system or a magnetic resonance imaging (MRI) system or a positron emission tomography (PET) system or a C-arm system or any combination thereof, for example, a PET-CT system. The medical imaging examination may be, for example, a computed tomography (CT) examination or a magnetic resonance imaging (MRI) examination or a positron emission tomography (PET) examination or a C-arm examination or any combination thereof, for example, a PET-CT examination. The medical imaging scan may be, for example, a computed tomography (CT) scan or a magnetic resonance imaging (MRI) scan or a positron emission tomography (PET) scan or a C-arm scan or any combination thereof, for example, a PET-CT scan.

According to a further embodiment of the present invention, a computer program including programming instructions is provided, wherein said programming instructions may be loaded into the computer system of a medical imaging system, wherein said programming instructions cause said computer system to carry out the method of an embodiment of the present invention. The computer program or computer program product may be written in any language readable by a medical imaging system. It may be loaded into a processing unit and may be stored on any digital storage medium. For example, the processing unit may be or may be part of or connected to the control unit as described herein.

A further embodiment of the present invention is directed to a non-transitory computer readable data storage medium encoded with programming instructions, wherein the programming instructions may be loaded into a computer system of a medical imaging system and cause said computer system to carry out the method according to embodiments of the present invention. The data storage medium may be any digital storage medium, for example a hard disc, a cloud, a medium connected to the computer system of a medical imaging system, or a portable medium such as an SD-card or SSD-card, a USB-stick, CD-ROM etc. All features and advantages of the method described herein are also applicable to the computer program and storage medium and vice versa. The method may be, for example, a computer-implemented method.

BRIEF DESCRIPTION OF THE DRAWINGS

Embodiments of the present invention will now be described with reference to the enclosed figures, in which:

FIG. 4 shows a flow diagram of an embodiment of a method according to the present invention.

DETAILED DESCRIPTION

Figure 1:
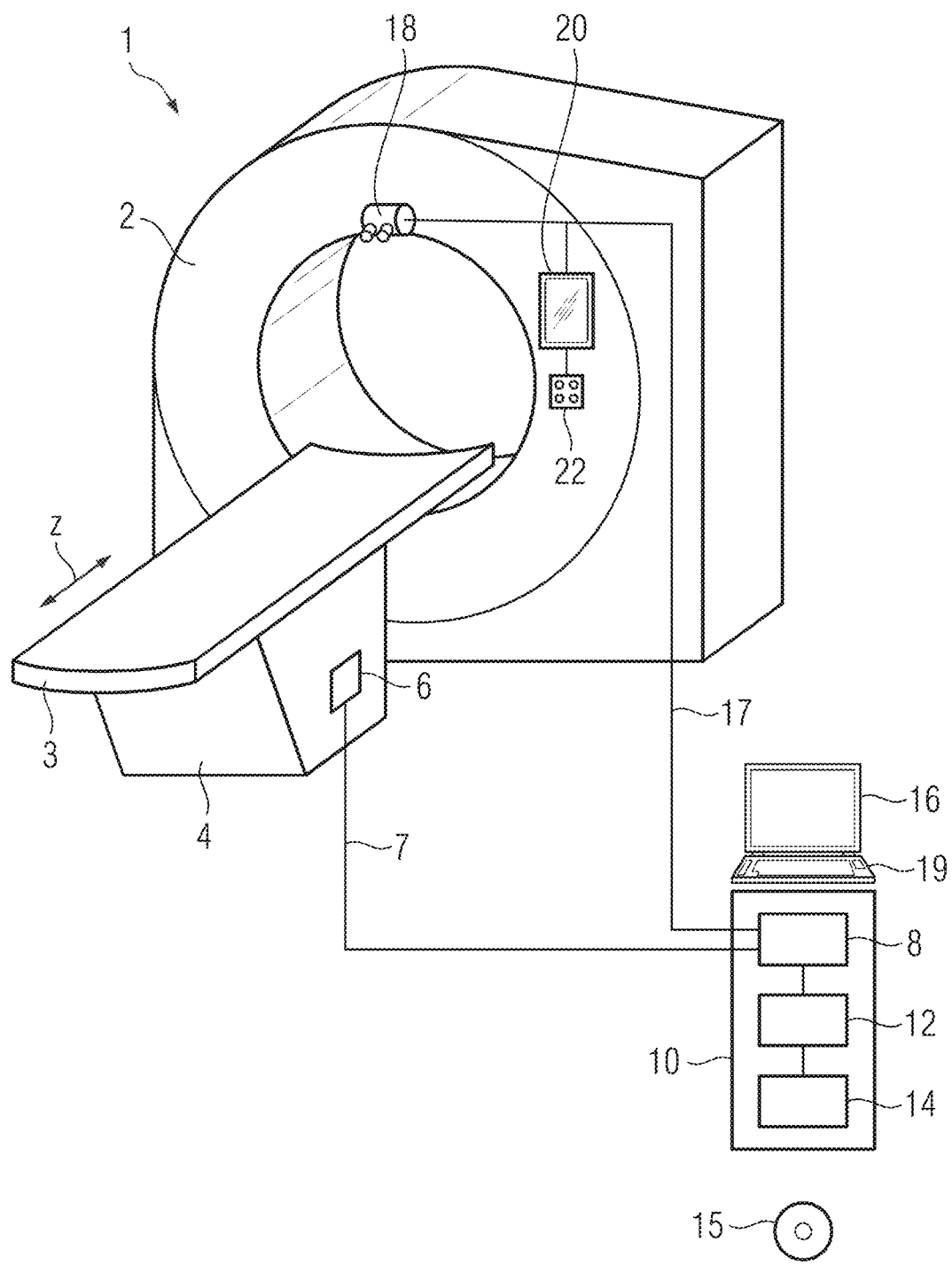
FIG. 1 shows a perspective view of a medical imaging system according to an embodiment of the present invention.

An embodiment of the present invention provides a method for controlling a medical imaging examination of a subject, wherein the medical imaging examination comprises performing a medical imaging scan of a body region of interest of the subject using a pre-selected scan protocol, wherein the medical imaging examination is performed using a medical imaging system having a gantry, a patient table which is moveable with respect to the gantry and on which the subject is positioned, a control unit for controlling the medical imaging scan and having access to an image sequence of the subject acquired by a camera, and wherein the method comprises the steps of receiving an image sequence of the subject from the camera during the medical imaging scan; receiving the current position and/or velocity of the patient table during the medical imaging scan; performing a motion tracking analysis of the received image sequence to extract a motion model, wherein the motion tracking analysis and/or the motion model is tailored to the body region of interest and takes into account the current patient table position and/or velocity; analysing the motion model to detect subject motion and, for example if the detected motion is above a pre-determined threshold, adapting the medical imaging examination to the detected motion and/or issuing an alert to make the subject and/or an operator of the medical imaging system aware of the detected motion.

The method uses a camera-based approach to track and quantify patient motion and further uses the intrinsic knowledge of the system about the scan protocol and/or the motion of the patient table to adequately adapt the medical imaging examination to the estimated patient motion.

The medical imaging examination may be any clinical medical imaging exam, including angiography or radiation therapy planning. The medical imaging examination may comprise one or several medical imaging scans, wherein each medical imaging scan acquires medical images from a body region of interest of the subject using a pre-selected scan protocol. The scan protocol may be pre-selected by the radiologist or a doctor ordering the medical imaging examination and may already specify the body region of interest, as well as scan parameters. The scan parameters may include the resolution, slice thickness, dose, radiation energy and whether or not contrast agent is to be applied. Thus, the scan protocol may be tailored to the diagnostic question (for example trauma, tumour, blood vessels, stroke), as well as the body region of interest on which the medical imaging scan is to be performed.

The medical imaging system has a gantry and a patient table which is moveable with respect to the gantry and on which the subject is lying, usually in a supine position. According to an embodiment, the gantry comprises an X-ray source and an X-ray detector, which are rotatable around the patient table. According to an embodiment, the gantry comprises a superconducting magnet in form of a hollow cylinder, into which the patient table can be inserted along an axial direction.

In some embodiments, the gantry is stationary, and the patient table is moveable at least in axial direction (z-direction) through the gantry. However, embodiments of the present invention are also applicable to medical imaging system with a moveable, e.g., slidable, gantry, wherein the patient table may be stationary or may also be moveable. Gantry and patient table are usually moveable at least in z-direction with respect to each other. The medical imaging system further comprises a control unit for controlling the medical imaging scan, which may be part of a computer system. The control unit has access to image sequences acquired by a camera disposed above the subject. The motion tracking analysis according to embodiments of the present invention may also be performed by the control unit, or by another processing unit, which may also be part of the computer system and which is connected via a data link to the control unit. Thus, the processing unit may be the or part of the control unit.

The camera may be fixed to the gantry and may be integrated into the medical imaging system. It may be disposed somewhere above the patient table. It may be mounted on a separate stand or at the ceiling above the patient table. Thus, the camera may be stationary with respect to the gantry, or alternatively with respect to the patient table. The camera may be an optical camera, in particular a digital or video camera capable of acquiring a time sequence of images of the patient while he is positioned on the patient table. The time resolution is preferably sufficient to capture relevant movement during the scan, for example 2-120 frames per second. The camera may be a camera already integrated in state-of-the art medical imaging systems, which today is used simply for visual patient monitoring. According to embodiments of the present invention, the control unit receives not only the image sequence from the camera during the medical imaging scan but is also aware of or receives the current position and/or velocity of the patient table, and optionally also the pre-selected scan protocol.

The control unit or processing unit then performs a motion tracking analysis of the received image sequence to extract a motion model of the body region of interest of the subject, wherein the motion tracking analysis and/or the motion model are tailored to the body region of interest and take into account the current patient table position and/or velocity. Thereby, the motion tracking analysis may be simplified and therefore stabilized, because based on the body region of interest and optionally the scan protocol to be applied, an appropriate, e.g., simplified motion model is applied. Already knowing the body region of interest also allows to detect the relevant body region on the images (which may have a larger field of view) beforehand.

In the next step, the motion model is analysed to detect subject motion. Preferably, the detected motion is classified as sufficient to compromise the scan process (e.g., above a pre-determined threshold) or as non-existent or irrelevant. For example, if the threshold is crossed (or always), the medical imaging system may adapt to the motion in a manner specific to the medical imaging examination and optionally scan protocol and/or body region.

Thus, a camera-based approach is presented to track and quantify patient motion and to adequately adapt the medical imaging examination to the estimated patient motion. The method exploits specific information available at the medical imaging system, such as the body region to be scanned and optionally the scan protocol to be applied, in order to adequately react to patient motion. The method also incorporates available motion information of the patient table. Embodiments of the present invention, thus, provide a method for mitigating the effect of patient motion, in which the scan workflow is not negatively impacted by additional devices or workflow steps to track patient motion.

The motion tracking analysis may utilise machine-learning based algorithms to estimate motion on the image sequence. For example, algorithms provided by Google MediaPipe (currently available under https://mediapipe.dev) may be used. The algorithms use e.g., neural networks, to extract the position of pre-determined objects on each image. Thereby, motion can be estimated directly from the RGB image data, or in the case of a three-dimensional (3D) camera acquiring images with depth information, also form the depth data. In low-end medical imaging systems, where only two-dimensional (2D) cameras are available, the motion tracking analysis may include deriving the motion from the 2D image sequences using a state-of-the art algorithms. By taking into account the current patient table position and/or velocity, the motion may be corrected for movements of the medical imaging system patient table, that are explicitly known within the control unit. One correction approach is to subtract the table motion from the camera-estimated overall motion. This ensures that only patient motion relative to the table is captured by the camera-based motion estimates.

According to an embodiment, the motion tracking analysis uses a motion model which is specific to the selected scan protocol and/or the body region of interest. In some embodiments, the selected scan protocol already comprises the relevant body region, wherein the body region of interest may for example be head, thorax, a limb or part of a limb, hip, neck, shoulder, or any other body part which may be covered by a medical imaging scan. The motion model may be tailored to the shape, the features and/or the kind of motion that may occur in the specific body region. In particular, the motion model may consider the joints and the movement they allow. For example, the head may, in a first approximation, be taken as a rigid body, i.e., it can rotate and possibly translate, but the skull cannot deform within itself. In a second approximation, movements of the jaw and throat, such as swallowing, may be incorporated into the model. Motion models of the limbs may incorporate the possible movement at the joints, whereas a motion model of the thorax will include breathing motion and optionally the heartbeat. Thus, the motion tracking analysis will specifically look out for motion which fits the motion model specific to the body region of interest to be scanned.

The default/general motion model may be a dense, elastic motion field capturing the motion at each image position.

When the motion model is specific to the body region of interest, the motion tracking analysis may comprise detecting and tracking landmarks specific to the body region of interest in the image sequence, applying a filter algorithm to the tracked landmarks to compensate inaccurate detections in one or several of the images of the sequence, in particular a Kalman filter; correcting the tracked landmarks by the position and/or velocity of the patient table; and estimating the motion model based on the filtered and corrected landmarks.

The landmarks can be detected for example by an algorithm based on a trained neural network. Thus, an appropriate number of landmarks (e.g., 6-300, preferably 40-150) may be pre-defined for each specific body region, wherein the landmarks designate characteristic portions of the body surface. If the body region is the head, the landmarks may be facial landmarks, which may be used to determine the position of the eyes, nose, and mouth.

Since the landmarks are detected in each image of the sequence independently of each other, errors in the detection may lead to abrupt changes from on image to the next, leading to instability. Therefore, a filter algorithm may be applied to the tracked landmarks to compensate inaccurate detections in one or several of the images. In one embodiment, this may be a Kalman filter, as described for example in G. Welch and G. Bishop "An Introduction to the Kalman Filter", Sep. 17, 1997. A Kalman filter is an algorithm that uses a series of measurements observed over time (here: the positions of the tracked landmarks) containing statistical noise and other inaccuracies, to produce estimates of unknown valuables (here: the positions of tracked landmarks on later/future images in the series) that tend to be more accurate than those based on a single measurement alone. By using a Kalman filter, the motion of the tracked landmarks can be estimated with higher certainty and stability. An alternative algorithm is the Sparse Optical Flow algorithm, for example, as described in J. Barron, D. Fleet and S. S. Beauchemin "Performance of Optical Flow Techniques", International Journal of Computer vision 12, 43-77 (1994). This technique may be used to approximate the 2D motion field, i.e., the projection of 3D velocities onto the imaging surface, from the image intensity of the image sequence.

Since the subject motion is being tracked during a medical imaging scan, table movement is expected. To ensure that only the movement of the body region of interest, for example the head, is detected, the positions of the tracked landmarks may be corrected according to the patient table movement. These table movements (position and/or velocity including the direction) are explicitly known within the medical imaging system, e.g., in the control unit. Thus, based on the filtered and corrected landmarks, a motion model specific to the body region can be estimated. In an embodiment, the motion vectors of the landmarks constitute the motion model.

According to an embodiment, the motion tracking analysis further comprises estimating rotation and translation vectors on the basis of the positions of the landmarks on each image of the sequence and the camera parameters, determining the orientation and movement of the body region of interest, in particular the head, based on the detected landmarks and the rotation and translation vectors. From the position of the landmarks and the known intrinsic parameters of the camera, in particular the camera's position and orientation with respect to the patient table, rotation and translation vectors can be estimated. These translation and rotation vectors may for example apply to a body region which may be assumed to be a rigid body, such as the head. In this case, only 6 degrees of freedom (three translation vectors and the three Euler angles) need to be estimated for each time point.

For this purpose, a direct linear transform solution with the known intrinsic parameters of the camera could be applied. In this process, each landmark of the body of interest in the world coordinate system is projected onto the image plane to consider the orientation and position of the body from an image sequence to the camera. To minimize projection errors, a Levenberg-Marquart optimisation could be applied to iteratively adjust the rotation and translation vectors. Furthermore, the resulting vectors and the intrinsic parameters of the camera may be used to calculate the Euler angles. Consequently, the orientation and movement of the head may be checked based on the determined facial landmarks, vectors and angles.

According to an embodiment, the method comprises a step of correcting the motion model or the motion vector field by the patient table velocity. This may be done by correcting the motion model, in particular the position for the landmarks and motion vectors, by estimating the translation using the current position and/or velocity of the patient table. Thereby, the table motion in the images in the images may be compensated by shifting the image content by the table motion. Further, the control unit may identify the current patient table position, and only once the table position is close to the target position for the examination, the motion tracking analysis is started. In another embodiment, the threshold for motion recognition may be corrected by the patient table velocity.

According to an embodiment, the motion tracking analysis is started only once the patient table has reached a target position for the examination. Usually, the patient will lie down on the patient table while it is disposed outside the gantry, and then the patient table will be shifted at least in z-direction into the gantry, to a target position for this examination, e.g., such that the body region of interest is inside the gantry. By starting the motion tracking approach only once the patient table is at the target position, the calculation effort for correcting fast table motion may be reduced.

In the event that the body region is the thorax, the motion tracking analysis may comprise the extraction of a one-dimensional (1D) model of upwards and downwards motion of the thorax from the image sequence acquired by a three-dimensional camera. This implies that depth information is available, and in this case the upward/downward motion may provide an adequate model of breathing. For example, the motion tracking analysis may comprise a step of averaging the depth (i.e., distance from the camera) of the chest over a pre-defined area on each image of the sequence, and optionally using a Kalman filter to predict the further breathing motion. Since the breathing motion is cyclic, extrapolation of the movement is possible.

The motion tracking analysis may comprise a step of applying a dense motion tracking approach to the sequence of images to estimate a motion vector field, in particular by using an optical flow technique. This approach is advantageous in particular in case only 2-D camera motion tracking is available. This may be followed by correcting the motion vector field by the patient table velocity. From the motion field, the breathing motion may be extracted as follows:

According to an embodiment, the motion vector field is calculated first in a coarse resolution, followed by a calculation by one or several finer resolutions. In other words, the analysis may be performed in a multi-resolution fashion to obtain a global breathing model at a coarse level, but and detect further movements at the finer resolutions. In an example, the image sequence may have a resolution of 640×1080 pixels. However, in the first step, it is sampled to a much lower resolution, in order to estimate motion on a large scale first. This has the advantage that aliasing is suppressed. When the main movements have been identified, the analysis is repeated on a finer resolution, to further differentiate detected motion.

According to an embodiment, the motion tracking analysis may further comprise the steps of analysing the orientation of the motion vector field for detecting inward and outward motion, in particular by calculating the divergence of the motion vector field, and on this basis estimating a motion model of breathing motion.

This is based on the insight that inspiration and expiration can be differentiated by analysing the orientation of the motion vectors: at the sides of the body, inspiration, i.e., an expansion of the chest, is characterized by motion vectors pointing towards the boundaries of the image. During expiration, i.e., contraction of the chest, the motion vectors point towards the centre. Mathematically, this may be characterised by the divergence of the vector field, a positive value indicates an expansion of the chest (inspiration), a negative value indicating expiration.

Further, a secondary breathing motion in z-direction may be observed in the waist region or the shoulder region. For the shoulders, inspiration leads to a shift towards the head, whereas expiration leads to a movement towards the feet. At the waist, the motion may be upwards or downwards for inspiration, depending on whether chest or abdominal breathing is dominant. Nevertheless, the movement in z-direction at the waist may be valuable to support the detection of breathing and to differentiate between chest and abdominal breathing if the general phases of inspiration/expiration are detected from the body sides or the shoulders. The magnitude of the motion vector field describes the amount of breathing motion. The above-described multi-resolution analysis may be used to be able to differentiate between abdominal and chest breathing in the finer resolutions.

Based on the detected motion, in particular whether the motion crosses a threshold, the medical imaging system may react and adapt the medical imaging examination in on or more ways.

According to an embodiment, the medical imaging system may issue an alert to the subject and/or the operator. For example, the operator, i.e., a technician or radiological assistant, may receive a visual or acoustic warning. The visual warning can be realized as a colour overlay on the live image shown on the scanner tablet. The alert may include the kind of detected motion, and suggestions for action. For example, to re-position the patient, or to instruct the patient to counteract the movement. Alternatively, the subject may be made aware of the motion through a visual or acoustic warning. According to an embodiment, the alert issued to the subject may comprise the kind of motion and/or a suggestion for correcting the motion. For example, the alert may include a visual or acoustic sign to catch the subject's attention. Afterwards, one or more of the images acquired by the camera may be displayed to the subject on a screen, including arrows to indicate how the patient should move in order to correct the inadvertent motion. For example, there may be an arrow or an acoustic sign, asking him to turn his head back to the centre, when he/she before turned the head to one side.

According to another embodiment, adapting the medical imaging examination may comprise re-acquiring the medical imaging data which were compromised by the detected motion. The medical imaging data may be, for example, computed tomography data or magnetic resonance imaging data.

For example, the patient table may stop or move backwards to allow the medical imaging system to scan the affected portions again. This may be necessary for example when coughing is detected, which is possible using the inventive technique. In prior art techniques, only a respiratory surrogate (i.e., a simplified 1D signal) was detected via the chest belt, and this could not detect complex movement like coughing. By detecting couching in the camera-based inventive approach, re-scanning of certain z-positions may be triggered when necessary.

According to a further embodiment, adapting the medical imaging examination may comprise performing a motion-compensated image reconstruction of the medical imaging data (also referred to as motion-compensated medical image reconstruction), for example a motion-compensated filtered-back projection. In other words, the camera-based motion estimation may be used as input information for state-of-the-art motion-compensated reconstruction algorithms, like the algorithm by Dirk Schafer mentioned above, to correct the reconstruction for the estimated motion. The medical image reconstruction may be, for example, a computed tomography image reconstruction or a magnetic resonance image reconstruction.

According to an embodiment, the medical imaging examination is a computed tomography examination (also referred to as a CT examination), the medical imaging scan is a computed tomography scan (also referred to as a CT scan), and the medical imaging system is a computed tomography system (also referred to as a CT system).

In particular, a method for controlling a CT examination of a subject is disclosed herewith, wherein the CT examination comprises performing a CT scan of a body region of interest of the subject using a pre-selected scan protocol, wherein the CT examination is performed using a CT system having a gantry, a patient table which is moveable with respect to the gantry and on which the subject is positioned, a control unit for controlling the CT scan and having access to an image sequence of the subject acquired by a camera, and wherein the method comprises the steps of
(a) receiving an image sequence of the subject from the camera during the CT scan;
(b) receiving the current position and/or velocity of the patient table during the CT scan;
(c) performing a motion tracking analysis of the received image sequence to extract a motion model, wherein the motion tracking analysis and/or the motion model is tailored to the body region of interest and takes into account the current patient table position and/or velocity;
(d) analysing the motion model to detect subject motion and, for example if the detected motion is above a pre-determined threshold, adapting the CT examination to the detected motion and/or issuing an alert to make the subject and/or an operator of the CT system aware of the detected motion.

According to an embodiment, the medical imaging examination is a magnetic resonance imaging examination (also referred to as an MRI examination), the medical imaging scan is a magnetic resonance imaging scan (also referred to as an MRI scan), and the medical imaging system is a magnetic resonance imaging system (also referred to as an MRI system).

Embodiments of the present invention are further directed to a medical imaging system comprising a gantry, a patient table which is moveable with respect to the gantry, a camera disposed above the patient table in a known position and orientation with respect to the gantry, wherein the camera is adapted to acquire an image series of a subject positioned on the patient table, and a control unit for controlling a medical imaging scan. The control unit is adapted to receive an image sequence of the subject from the camera during the medical imaging scan, and the current position and/or velocity of the patient table during the medical imaging scan. The control unit is further adapted for performing a motion tracking analysis of the received image sequence to extract a motion model, wherein the motion tracking analysis and/or the motion model is tailored to the body region of interest and takes into account the current patient table position and/or velocity; and the control unit is further adapted for analysing the motion model to detect subject motion and, for example if the detected motion is above a pre-determined threshold, for adapting the medical imaging examination to the detected motion and/or for issuing an alert to make the subject and/or an operator of the medical imaging system aware of the detected motion.

The medical imaging system is adapted for performing the method according to embodiments of the present invention. All features and advantages described with respect to the method are also applicable to the medical imaging system and vice versa. The method may be (at least partly) carried out by a control unit, which is part of the medical imaging system, and which receives the image sequence, performs the motion tracking analysis, and may adapt the medical imaging examination to react to the detected motion.

According to an embodiment, the camera is a video camera or digital camera adapted to acquire 2-D. The camera may be integrated into the gantry. Thereby, the position and other intrinsic camera parameters, such as the field-of-view, the imaging angle with respect to the patient table, the resolution, etc. are automatically known to the medical imaging system, in particular the control unit.

According to an alternative embodiment, the camera inside is a 3D camera adapted to acquire images including depth information of the subject. Such 3D cameras may for example include two lenses in order to capture the body region of interest in two angles, and thereby extract contour/depth information.

The medical imaging system may be, for example, a computed tomography (CT) system or a magnetic resonance imaging (MRI) system or a positron emission tomography (PET) system or a C-arm system or any combination thereof, for example, a PET-CT system. The medical imaging examination may be, for example, a computed tomography (CT) examination or a magnetic resonance imaging (MRI) examination or a positron emission tomography (PET) examination or a C-arm examination or any combination thereof, for example, a PET-CT examination. The medical imaging scan may be, for example, a computed tomography (CT) scan or a magnetic resonance imaging (MRI) scan or a positron emission tomography (PET) scan or a C-arm scan or any combination thereof, for example, a PET-CT scan.

According to a further embodiment of the present invention, a computer program including programming instructions is provided, wherein said programming instructions may be loaded into the computer system of a medical imaging system, wherein said programming instructions cause said computer system to carry out the method of an embodiment of the present invention. The computer program or computer program product may be written in any language readable by a medical imaging system. It may be loaded into a processing unit and may be stored on any digital storage medium. For example, the processing unit may be or may be part of or connected to the control unit as described herein.

A further embodiment of the present invention is directed to a non-transitory computer readable data storage medium encoded with programming instructions, wherein the programming instructions may be loaded into a computer system of a medical imaging system and cause said computer system to carry out the method according to embodiments of the present invention. The data storage medium may be any digital storage medium, for example a hard disc, a cloud, a medium connected to the computer system of a medical imaging system, or a portable medium such as an SD-card or SSD-card, a USB-stick, CD-ROM etc. All features and advantages of the method described herein are also applicable to the computer program and storage medium and vice versa. The method may be, for example, a computer-implemented method.

FIG. 1 shows a medical imaging system according to an embodiment of the present invention, which is adapted to carry out the inventive method. The medical imaging system 1 comprises a ring-shaped gantry 2. A patient table 3 is disposed on a foot 4 and can be moved in z-direction through the gantry via an actuator 6, which may include and electric motor, and which is connected by a data link 7 with control unit 8. The control unit 8 is part of computer system 10, which may further comprise a processing unit 12 and a data storage 14, such as a hard disc. A computer program product stored on CD-ROM 15 may be loaded into the computer system 10. The computer system 10 may have the user interface, for example in the shape of a screen 16 and a keyboard 19. The control unit 8 further controls the operation of the medical imaging system 1, in particular the gantry 2. It is also connected via a data link 17 with a camera 18 which is disposed on the housing of the gantry above the patient table 3. The control unit 8 may further be connected with a tablet 20, on which the images taken by the camera 18 may be visualized, as well as a user input device 22, which may have the shape of a remote control. The data links 7 and 17 may be cable-bound, but also may be wireless, for example by Bluetooth, WIFI or other data connections. The control unit 8 and/or the computer system 10, or the processing unit 12 may be situated remote from the medical imaging system, so the that the data links 7 and 17 are via one or more telecommunication systems or links, or via the internet.

Figure 2:
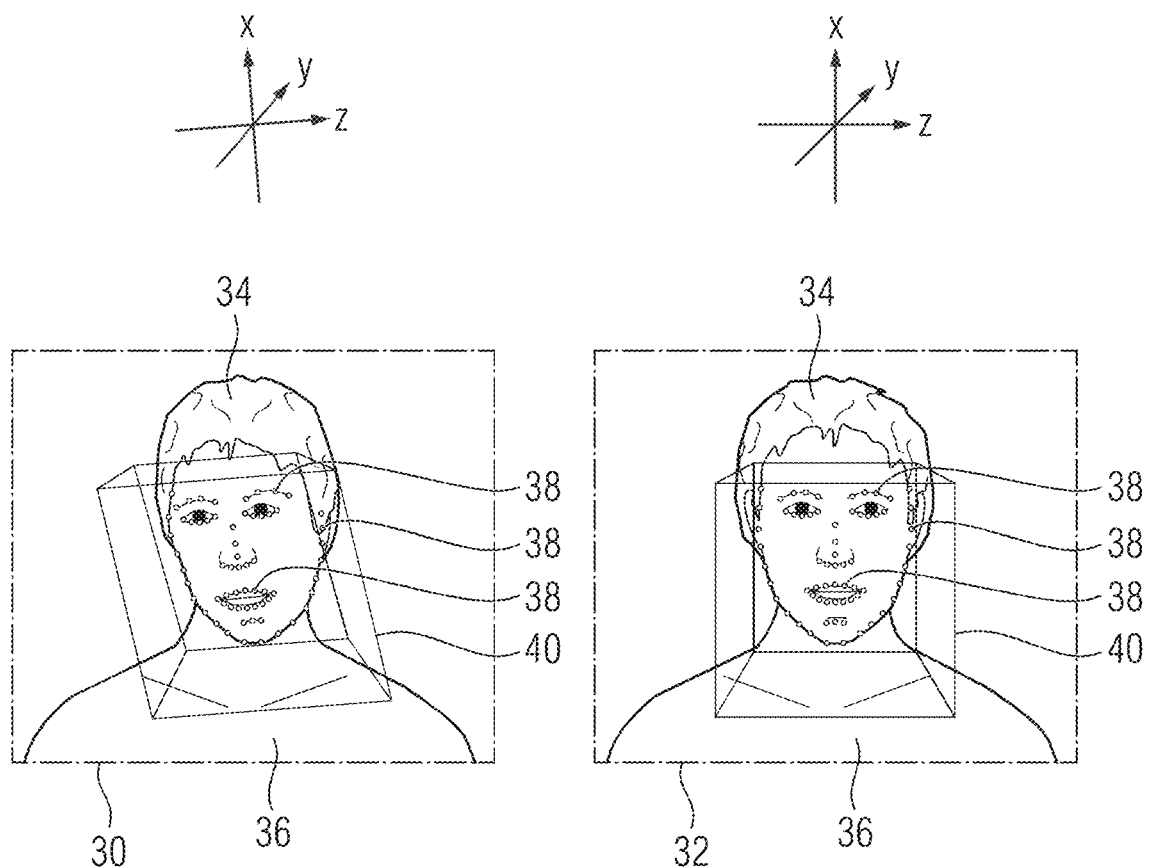
FIG. 2 shows an example of a motion model specific to the head, illustrated on two images acquired by a camera disposed above the patient table, the images showing the head and shoulders of a subject in two different motion states.

FIG. 2 illustrates the motion tracking analysis tailored to the head as the body region of interest. FIG. 2 shows two images, 30 on the left and 32 on the right, of a head 34 of a subject 36 lying on the patient table 3 beneath the camera 18. On each image acquired by the camera, a number of pre-determined facial landmarks 38 is detected, shown as dots 38. The facial landmarks outline the contour of the head, as well as the distinctive features of the face such as eyes, nose, and mouth. If the patient table 3 is moving, the position of the landmarks may be corrected according to the known movement of the patient table 3, which is recorded by actuator 6 and forwarded to control unit 8. From the facial landmarks 38, and taking into account the known intrinsic parameters of the camera, the motion tracking analysis with the direct linear transform solution followed by a Levenberg-Marquart optimization will calculate the axes of the head on each image, for example the longitudinal axis x, the front-to-back axis y, and the left-to-right axis z. These axes are illustrated by cube 40 on each image.

Figure 3:
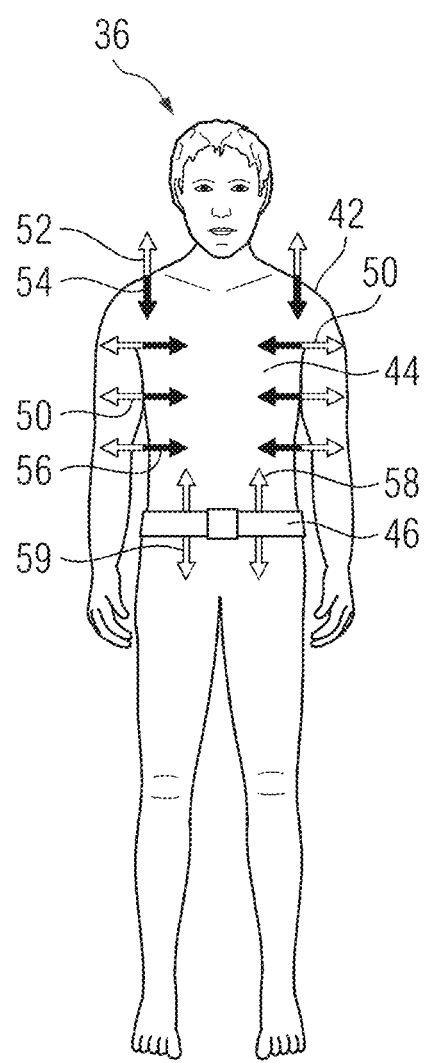
FIG. 3 shows a motion model tailored to breathing, illustrated on a schematic representation of a prone body.

For thorax scans, especially if only 2D camera motion tracking is available, a general dense motion tracking approach such as Optical Flow is applied to firstly estimate a motion vector field. From this motion field, the breathing motion is extracted as follows: the estimated motion vectors, as illustrated in FIG. 3, are first corrected by the known table motion. Now looking at FIG. 3, the motion model is illustrated on a schematic top view of a patient 36, in particular his shoulders 42, chest 44 and waist/belt 46. During inspiration, i.e., expansion of the chest 44, the sides of the body move outwards as illustrated by motion vectors 50. The shoulders move upwards, see vectors 52. During expiration, the shoulders move downward, see vectors 54, and the chest inwards, see motion vectors 56. Mathematically, this can be shown by calculating the divergence of the vector field, with expansion of the chest having a positive divergence, expiration being characterized by a negative divergence.

In order to distinguish chest and abdominal breathing, the motion at the waist or belt 46 may be further analysed: chest breathing is characterized by upwards movements 58, abdominal breathing by downward motion 59. Thus, the main value of analysing the motion fields at the waist is to support the detection of breathing, and to differentiate between the chest and abdominal breathing. The motion vector field is preferably extracted from the colour image of the subject and may be performed in a multi-resolution fashion to obtain a global breathing model at a course level, but still be able to differentiate for example between abdominal and chest breathing on the finer scales.

FIG. 4 illustrates an embodiment of the method of the present invention. In step 60, the patient is positioned onto the patient table 3, and the medical imaging examination is begun. And operator will select a scan-protocol and a body region of interest. In the next step 62, the camera will start acquiring images and send the image sequence of the subject to the control unit 8. When the patient table 3 begins to move by actuator 6, also the current position and motion of the patient table will be sent to the control unit 8 in step 64. The control unit 8 or the processing unit 12 will perform the motion tracking analysis 66 of the received image sequence and extract the specific motion model, which is tailored to the specific body region. At the same time, the medical imaging scan 68 is going on, in particular the patient table 3 is slowly moving through the gantry 2 while medical imaging data is acquired. In step 70, the motion model is analysed to detect subject motion and possibly adapt the medical imaging examination to the detected motion, as illustrated by arrow 72, by which a part of the scan 68 may be repeated at a certain z-position in which motion occurred. The steps 64, 66 and 70 are generally ongoing during the scan 68, at least steps 62 and 64. Preferably also the motion tracking analysis 66 and the analysis of the motion model 70 is occurring in real time, because this allows the medical imaging system to issue an alert to make the subject or the operator aware of the detected motion, as indicated at 74. Such an alert may for example be a sound signal and/or a visual indication of how the subject should move back into his initial position.

At 76, the medical imaging scan 68 is completed, and a reconstruction of the images may be performed, optionally taking into account the calculated motion model.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been disclosed in the form of embodiments and variations thereon, it will be understood that numerous additional modifications and variations could be made thereto without departing from the scope of the present invention.

What is claimed is:

1. A method for controlling a medical imaging examination of a subject, the medical imaging examination including performing a medical imaging scan of a body region of interest of the subject using a scan protocol, the medical imaging examination being performed using a medical imaging system having a gantry, a patient table configured to move with respect to the gantry and on which the subject is positioned, and a control unit configured to control the medical imaging scan and access an image sequence of the subject acquired by a camera, the method comprising:

receiving an image sequence of the subject from the camera during the medical imaging scan;

receiving at least one of a current position or a current velocity of the patient table during the medical imaging scan;

performing a motion tracking analysis of the image sequence to extract a motion model, wherein at least one of the motion tracking analysis or the motion model is tailored to the body region of interest and takes into account the at least one of the current position or the current velocity of the patient table;

analysing the motion model to detect motion of the subject; and in response to the detected motion being above a threshold, at least one of adapting the medical imaging examination to the detected motion or issuing an alert to make at least one of the subject or an operator of the medical imaging system aware of the detected motion.

2. The method of claim 1, wherein the motion tracking analysis uses a motion model, which is specific to at least one of the scan protocol or the body region of interest.

3. The method of claim 1, wherein the motion tracking analysis comprises:

detecting and tracking landmarks specific to the body region of interest in the image sequence;

applying a filter algorithm to the landmarks to compensate for inaccurate detections in one or more images of the image sequence;

correcting the landmarks by the at least one of the current position or the current velocity of the patient table; and estimating the motion model based on the filtered and corrected landmarks; wherein the filter algorithm is a Kalman filter.

4. The method of claim 3, wherein the motion tracking analysis comprises:

estimating rotation and translation vectors based on positions of the landmarks on each image of the image sequence and parameters of the camera; and determining an orientation and movement of the body region of interest based on the landmarks and the rotation and translation vectors; wherein the body region of interest is the head of the subject.

5. The method of claim 1, wherein the motion tracking analysis is started only once the patient table has reached a target position for the medical imaging examination.

6. The method of claim 1, wherein the motion tracking analysis comprises:

correcting the motion model by estimating a translation using the at least one of the current position or the current velocity of the patient table; wherein the correcting the motion model includes correcting a position of landmarks and motion vectors.

7. The method of claim 1, wherein the body region of interest is the thorax, the camera is a three-dimensional camera, and the motion tracking analysis includes extracting a one-dimensional model of upwards and downwards motion of the thorax from the image sequence.

8. The method of claim 1, wherein the motion tracking analysis comprises:

applying a dense motion tracking approach to the image sequence to estimate a dense motion vector field, wherein the dense motion vector field is calculated first in a coarse resolution, and then in one or more finer resolutions, and the dense motion tracking approach is an Optical Flow Technique.

9. The method of claim 8, wherein the body region of interest is the thorax, and the motion tracking analysis includes analysing an orientation of the dense motion vector field for detecting inward and outward motion of the dense motion vector field, and estimating a motion model of breathing motion, wherein the analysing an orientation of the dense motion vector field includes calculating a divergence of the dense motion vector field.

10. The method of claim 1, wherein the alert issued to the subject includes at least one of a kind of motion or a suggestion for correcting the motion.

11. The method of claim 1, wherein adapting the medical imaging examination comprises:

re-acquiring medical imaging data compromised by the detected motion.

12. The method of claim 1, wherein adapting the medical imaging examination comprises:

performing a motion-compensated medical image reconstruction.

13. The method of claim 1, wherein the medical imaging examination is a computed tomography examination, the medical imaging scan is a computed tomography scan, and the medical imaging system is a computed tomography system.

14. The method of claim 1, wherein the medical imaging examination is a magnetic resonance imaging examination, the medical imaging scan is a magnetic resonance imaging scan, and the medical imaging system is a magnetic resonance imaging system.

15. A non-transitory computer-readable storage medium encoded with programming instructions, wherein the programming instructions are loadable into a computer system of a medical imaging system and, when executed, cause said computer system to carry out the method of claim 1.

16. A medical imaging system adapted to perform a medical imaging examination of a subject, the medical imaging examination including a medical imaging scan of a body region of interest using a scan protocol, the medical imaging system further adapted to perform the method according to claim 1, and the medical imaging system comprising:

a gantry;

a patient table configured to move with respect to the gantry;

a camera in a position and orientation with respect to the gantry, the camera configured to acquire an image series of a subject positioned on the patient table; and a control unit configured to control a medical imaging scan, the control unit further configured to receive an image sequence of the subject from the camera during the medical imaging scan, receive at least one of a current position or a current velocity of the patient table during the medical imaging scan, perform a motion tracking analysis of the image sequence to extract a motion model, wherein at least one of the motion tracking analysis or the motion model is tailored to the body region of interest and takes into account the at least one of the current position or the current velocity of the patient table, analyze the motion model to detect motion of the subject, and in response to the detected motion being above a threshold, at least one of adapt the medical imaging examination to the detected motion or issue an alert to make at least one of the subject or an operator of the medical imaging system aware of the detected motion.

17. The medical imaging system of claim 16, wherein the camera is (i) a video camera or digital camera configured to acquire two-dimensional images or (ii) a three-dimensional camera configured to acquire images including depth information of the subject.

18. The medical imaging system of claim 16, wherein the medical imaging examination is a computed tomography examination, the medical imaging scan is a computed tomography scan, and the medical imaging system is a computed tomography system.

19. The medical imaging system of claim 16, wherein the medical imaging examination is a magnetic resonance imaging examination, the medical imaging scan is a magnetic resonance imaging scan, and the medical imaging system is a magnetic resonance imaging system.

* * * * *